(12) United States Patent
Horn et al.

(10) Patent No.: US 7,910,877 B2
(45) Date of Patent: Mar. 22, 2011

(54) MASS SPECTRAL ANALYSIS OF COMPLEX SAMPLES CONTAINING LARGE MOLECULES

(75) Inventors: David M Horn, Palo Alto, CA (US); Xiangdong Don Li, Union City, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 314 days.

(21) Appl. No.: 12/263,210

(22) Filed: Oct. 31, 2008

(65) Prior Publication Data

US 2010/0108876 A1    May 6, 2010

(51) Int. Cl.
*G06F 3/00* (2006.01)
(52) U.S. Cl. ............. 250/282; 250/281; 250/288; 702/2; 702/22; 702/30
(58) Field of Classification Search .................. 250/281, 250/282; 702/2, 22, 30
See application file for complete search history.

(56) References Cited

U.S. PATENT DOCUMENTS

| 7,653,496 B2 * | 1/2010 | Li ................................... 702/30 |
| 2003/0139885 A1 * | 7/2003 | Brock et al. .................... 702/19 |
| 2007/0176088 A1 * | 8/2007 | Li ................................. 250/282 |

OTHER PUBLICATIONS

Ferrige, A.G. et al., Maximum Entropy Deconvolution in Electrospray Mass Spectrometry, Rapid Communications in Mass Spectrometry, 1991, pp. 374-379, vol. 5.

Mann, Matthias et al., Interpreting Mass Spectra of Multiply Charged Ions, Analytical Chemistry, Aug. 1, 1989, pp. 1702-1708, vol. 61, No. 15.

* cited by examiner

*Primary Examiner* — David A Vanore
(74) *Attorney, Agent, or Firm* — Ping Hwung

(57) ABSTRACT

The present invention provides, inter alia, methods of analyzing mass spectral data based on charge states of analyte ions. In some embodiments, the methods can be used for differential profiling of samples, such as comparing a sample comprising a given compound and a sample comprising metabolites of the same compound. The methods can also be used to identify and isolate biomarkers. Systems for performing the methods, as well as computer-readable media for performing the methods, are also described.

16 Claims, 4 Drawing Sheets

MASS SPECTRAL ANALYSIS OF COMPLEX SAMPLES CONTAINING LARGE MOLECULES

BACKGROUND

Mass spectrometry is an analytical tool that can be used to determine the molecular weights of chemical compounds by generating ions from the chemical compounds, and separating these ions according to their mass-to-charge ration (m/z). The ions are generated by inducing either a loss or a gain of a charge by the chemical compounds, such as via electron ejection, protonation, or deprotonation. The ions are then separated according to their m/z values and detected. The resulting data are often presented as a spectrum, a two-dimensional (2-D) plot with m/z ratio on the x-axis and abundance of ions on the y-axis. Thus, this spectrum shows the distribution of m/z values in the population of ions being analyzed. This distribution is characteristic for a given compound. Therefore, if the sample is a pure compound or contains only a few compounds, mass spectrometry can reveal the identity of the compound(s) in the sample.

A complex sample usually contains too many chemical compounds to be analyzed meaningfully by mass spectrometry alone, because ionization of different chemical compounds may result in ions with the same m/z value. The more chemical compounds a sample contains, the more likely ions of the same m/z values will be generated from different compounds. Therefore, a complex sample is typically resolved to some extent prior to mass spectrometry, such as by liquid chromatography, gas chromatography, or capillary electrophoresis. In this sample separation step, the chemical compounds in the sample are separated based on how long they stay in the sample separation medium. Once a chemical compound goes through the sample separation medium, it enters a mass spectrometer system, and the ionization/ion separation/detection process begins as described above. The resulting data for each ion thus has one more property, retention time, which is the time the chemical compound that gives rise to the ion stays in the sample separation medium. Thus, mass spectral data of a sample that is analyzed by a sample separation method before mass spectrometry can be presented as a three-dimensional (3-D) plot, with retention time, m/z value and ion abundance on the three axes of the plot.

Even with a sample separation method, it is still not an easy task to analyze mass spectral data from a complex sample due to the vast number of peaks. A method has been introduced to deconvolute mass spectral data based on compound properties such as isotopic clusters (see U.S. Patent Application Publication 2007-0176088). In this method, 3-D peaks that share the same retention time are examined, and isotopic clusters of the same compound are grouped together, thereby reducing the complexity of the mass spectral data significantly. This method, however, is most useful for analytes with relatively small molecular weights. Large molecules, such as most intact proteins, are often too large for their isotopomers to be resolved in a mass spectrometer. As a result, an accurate monoisotopic mass cannot be calculated for the given isotopic cluster using the charge state spacing of the isotopomers.

Currently, the most common method for intact protein mass determination is the maximum entropy deconvolution method (Ferrige et al., 1991). This method transforms a mass spectrum in m/z units, usually by averaging all the spectra across an LC or other elution profile for a protein, to a mass spectrum containing the zero-charge representation of intact proteins (in Dalton units) across a user-specified mass range. For simple averaged mass spectra with at most a few intact proteins, this method is quite reliable. However, more complex mass spectra produce false positive "overtone" peaks, which correspond to masses calculated from randomly dispersed peaks from the raw data. This can be somewhat overcome by the user specifying a very wide mass range, but the algorithm would require a significantly longer amount of time to complete. Since maximum entropy deconvolution works on a mass spectrum but most proteins are characterized by LC/MS, a conversion from 3-D data (m/z, retention time, abundance) to 2-D data (m/z, abundance) is critical for optimum performance of the algorithm. For simple data, the selection of the averaged spectrum is quite easy since each eluting protein should show an isolated peak in the LC chromatogram. However, for very complex mixtures, the selection of the optimal range of spectra to average is nearly impossible, since many proteins will be closely eluting or co-eluting. Finally, the abundance values in maximum entropy deconvoluted spectra are not reliable from run to run, making relative quantitation between experiments impossible.

Therefore, it is desirable to have a better method for deconvoluting complex mass spectral data from samples comprising large molecules.

DESCRIPTION OF THE INVENTION

Figure 1:
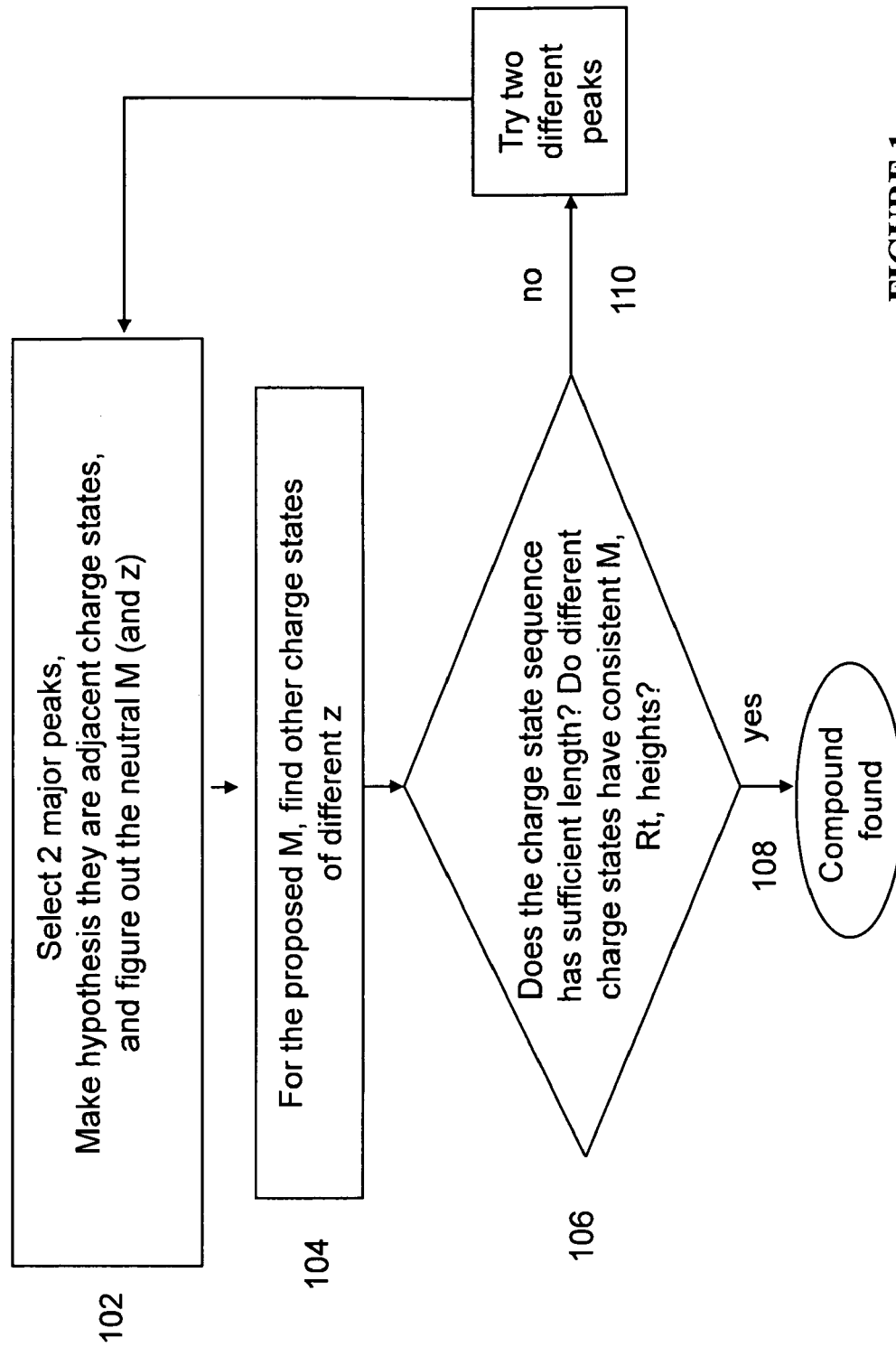
FIG. 1 shows a method of identifying peaks that correspond to different charge states of the same compound. "Neutral M" is the proposed molecular weight of a molecule that gave rise to the selected peaks. z, number of charge(s). Rt, retention time.

The present invention relates to, inter alia, methods for analyzing mass spectral data from a complex sample based on charge states of the different ions derived from the same molecule. The methods can be applied broadly, including differential profiling of multiple samples.

Various embodiments of the present invention will be described in detail with reference to the drawings, wherein like reference numerals represent like parts throughout the several views. Reference to various embodiments does not limit the scope of the invention, which is limited only by the scope of the claims attached hereto. Additionally, any examples set forth in this specification are not intended to be limiting and merely set forth some of the many possible embodiments for the claimed invention.

Prior to describing the invention in further detail, the terms used in this application are defined as follows unless otherwise indicated.

DEFINITIONS

Unless defined otherwise, all technical and scientific terms used herein have the same meaning as commonly understood to one of ordinary skill in the art to which this invention belongs. Although any methods, devices and material similar or equivalent to those described herein can be used in the practice or testing of the invention, the preferred methods, devices and materials are now described.

As used herein, the term "differential profiling" or "differential display" refers to investigating the differences between the mass spectral data for a first sample and those for a second sample. Similarly, differential profiling can be performed for more than two sets of data, namely comparing the mass spectral data of three or more samples and investigating the differences among them. It should be noted that sometimes differential profiling is performed using sample sets, each of which comprises multiple samples. For instance, a user may wish to compare the molecules in the sera of breast cancer patients and those in the sera of normal controls. Thus, serum samples from multiple breast cancer patients are obtained, and serum samples from multiple normal controls are also collected. Each sample is analyzed, and differential profiling is conducted to compare the mass spectral data of the samples in the patient group to the mass spectral data of the control group. A differential display image or plot shows the differences between or among the samples, with respect to abundance of a particular component, presence of a particular chemical species, or changes in expression level of a particular component.

The term "sample" as used herein relates to a material or complex mixture of materials, typically, although not necessarily, in fluid form. Samples of the present invention include, but are not limited to, biological samples obtained from natural biological sources, such as cells or tissues, or plants. The samples of the present invention include, but are not limited to, complex biological samples containing many different components or metabolites, such as urine or serum, for example. The samples of the present invention also include complex mixtures derived from non-animal sources, such as complex extracts derived from plants. The sample may also be non-biological, such as environmental samples (water, air, rain, etc.)

The term "spectral peak" refers to a peak in the output from any type of spectral analysis instrument, and is known in the art. In a given analysis, peaks can represent one or more components in a sample. A "mass spectral peak" is a spectral peak in a mass spectrum.

The term "3-D peak" refers to a cluster of LC-MS (or GC-MS, CE-MS, etc.) signals that have the same m/z value (subject to variations in measurement), and similar retention time values. The signals could be either raw profile spectral pixels or spectral peaks.

In this specification and the appended claims, the singular form "a," "an," and "the" include plural reference unless the context clearly dictates otherwise. Unless defined otherwise, all technical and scientific terms used herein have the same meaning as commonly understood to one of ordinary skill in the art to which this invention belongs.

Deconvolution of Complex Mass Spectral Data Using Large Molecule Feature Extraction (LMFE)

Large molecules, such as most intact proteins, are often too large for their isotopic clusters to be resolved into their individual isotopomers on a mass spectrometer. Currently, the most common method for intact protein mass determination is the maximum entropy deconvolution method (Ferrige et al., 1991). However, as discussed above, the maximum entropy deconvolution method is not efficient, or even suitable, for complex samples.

To resolve the problem, an aspect of the present invention provides a method for analyzing complex samples that contain large molecules based on charge states of the analyte molecules. Large molecules, such as intact proteins, are typically ionized to multiple charge states because they have multiple atoms and functional groups that can be ionized. When a compound of mass M ("neutral mass") is ionized to form multiple ions, the m/z value of each resulting ion is the mass of the ion divided by the number of charges of the ion, which can usually be expressed as follows (see, e.g., Mann et al., 1989):

$$m/z = (M \pm im_a)/|i| \quad (1),$$

where i is the charge state of the ion, and $m_a$ is the mass of the charged moiety that was added to or removed from the compound to result in ionization. When the charged moiety has a positive charge, the sign is +, and the numerator (the mass of the ion) is $M+im_a$. When the charged moiety has a negative charge, the sign is –, and the numerator is $M-im_a$. For example, after addition of two protons in a protonation event, i is +2, $m_a$ is the mass of a proton ($m_a$=1.0073), and m/z=(M+2×1.0073)/2. As another example, after removal of an electron from the molecule, i is +1, $m_a$ is the mass of an electron ($m_a$=5.446×10$^{-4}$), and m/z is (M–5.446×10$^{-4}$)/1. Note that a skilled artisan would know that when the charged moiety has multiple charges, the formula has to be modified. For example, if the charged moiety has a charge of +2, such as $Ca^{++}$, the formula should be $m/z=(M+(i/2)m_a)/i/$.

Thus, a large molecule results in multiple ions with varying m/z values (varying according to formula (1) above) but share the same retention time, because the ions are generated from the same compound. The present invention utilizes this relationship to analyze mass spectral data from complex samples. One aspect of the present invention thus provides a method of deconvoluting complex mass spectral data by grouping together 3-D peaks that have the same retention time and related m/z values. The m/z values of these peaks are related according to formula (1). As a result, the complex mass spectra data are simplified to groups of peaks, each group corresponding to a compound.

A person of ordinary skill in the art would know how to identify co-eluting 3-D peaks of which the m/z values relate to one another as described above. FIG. 1 illustrates an exemplary method. This method is based on the observation that the multiple ions derived from the same compound are smoothly distributed. In other words, when the intensities of the ions are plotted against the charge states of the ions, any two adjacent charge states would have relatively similar intensities as compared to two randomly selected charge states. In this method, to identify different charge states of the same compound, two major peaks are selected from the data set and postulated as adjacent charge states of the same compound. Accordingly, their m/z values would be related:

$$m/z \text{ value of one peak} = (M+im_a)/|i|$$

$$m/z \text{ value of the other peak} = (M+(i+1)m_a)/|i+1|$$

Figure 2:
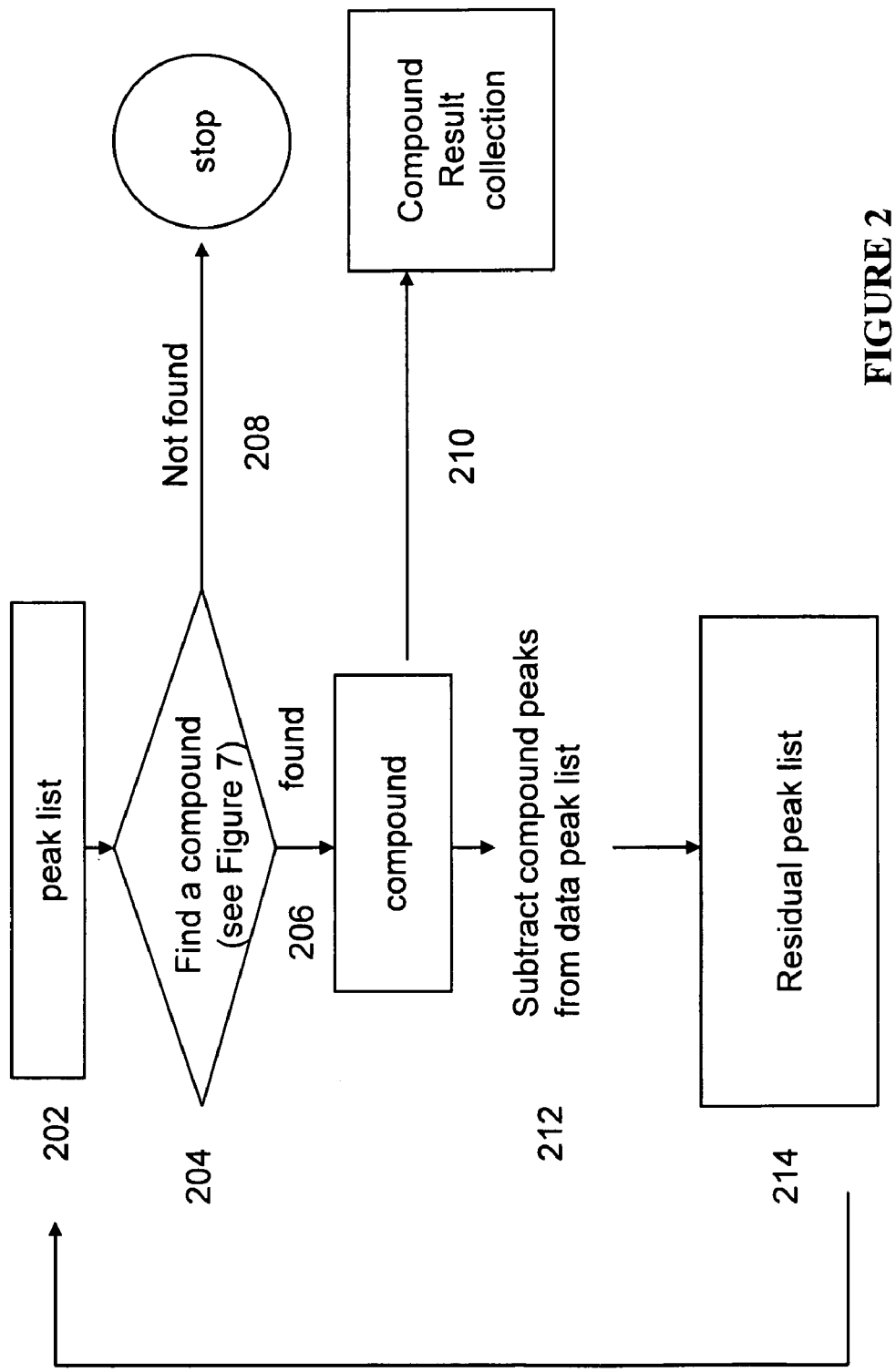
FIG. 2 shows a method of deconvoluting a data set (peak list) by grouping compound peaks that correspond to the same compound.

Since the m/z values are known, M and i can be calculated from the equations above. A person of ordinary skill in the art would know $m_a$ is the mass of one of a few candidate charged moieties, such as proton, $Na^+$, $K^+$, or $NH_4^+$. The mass of each of the candidates is known in the art. In turn, the m/z values of other charge states of the proposed compound can be calculated from M and i, and compared to the data. If these other charge states exist in the data set in sufficient number and intensities, a compound is found and all the related peaks are removed from the data set. This process is then repeated using the residual data set to identify the next group (see FIG. 2). Whether there are sufficient charge states in the data set to justify the finding of a compound depends on the molecular weight of the proposed compound (M). When M is larger, more charge states need to identified in the data set; for instance, one more charge state is required for every 10 kDa mass increase. In general, at least five charge states should be found in the data set for a given M and $m_a$, more preferably 6, 7, 8, 9, 10, 11, 12, or more charge states. If a compound is not found, a different combination of two peaks would be selected to repeat this process in the original data set.

Similarly, $(M-im_a)/|i|$ and $(M-(i+1)m_a)/|i+1|$ should be used in the approach described above for negatively charged moieties, such as electron or the chloride ion.

Since the analysis methods based on isotopic clustering (see U.S. Patent Application Publication 2007-0176088) are primarily for small molecules and those based on charge states are primarily for large molecules, both methods can be used for the same data set if the sample contains, or is suspected to contain, both small and large molecules. For example, a data analysis program may give the user the option of analyzing small molecules or large molecules, and apply an appropriate method accordingly. If the user is interested in both small and large molecules, the program can employ both methods sequentially on the same set of data. In defining small or large molecules, the program may include pre-set molecular weight ranges for small and large molecules, and applies the large molecule method when the user selects a molecular weight within the large molecule range, and vice versa. The molecular weight range for large molecules is generally 4 kiloDaltons and larger, such as ≧5 kDa, ≧6 kDa, ≧7 kDa, ≧8 kDa, ≧9 kDa, ≧10 kDa, ≧12 kDa, ≧14 kDa, ≧16 kDa, ≧18 kDa or ≧20 kDa. The program may also include a function where, if after applying either the small or large molecule method, many spectral peaks are still not grouped, the program would apply the other method automatically, or offer the user the option of applying the other method.

Figure 3:
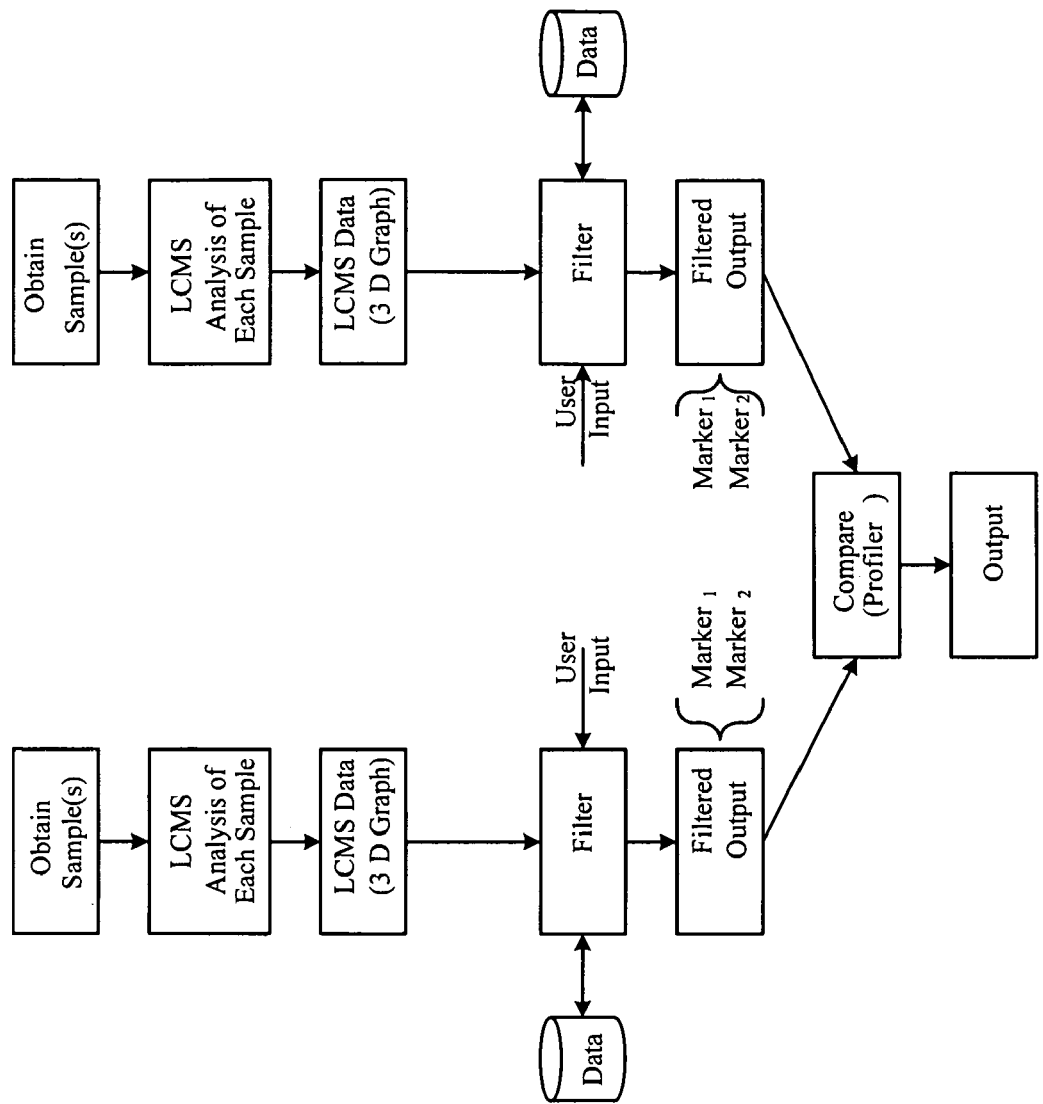
FIG. 3 is a diagram representing a method for the differential analysis of two complex biological samples.

The present invention also provides a method for differential analysis of components in different samples or groups of samples. An exemplary protocol is shown in FIG. 3. Thus, at least two samples are obtained and analyzed by LC/MS, yielding a set of LC/MS data (which can be displayed as a 3-D graph) per sample. Each data set is then analyzed by the methods described herein to group together peaks that belong to the same original molecule. During this analysis, the user may optionally set filters to retain only a portion of the data depending on the interest of the user, as is the case for the analysis of individual samples without differential profiling. For example, the user may limit the retention time, mass ranges, relative abundance, and/or nature of the molecules, to focus on the kinds of molecules the user wishes to study. The result from each sample, optionally filtered, is compared to one another, thereby identifying molecules of which the abundances change among different samples. These molecules are potentially markers that change according to the biological status of the samples.

The methods described herein can also be utilized to isolate compounds of interest. For example, after markers (compounds that change in abundancy between or among samples) are identified by differential profiling, their properties (retention time, mass, etc.) can be used as criteria for isolation and purification from samples. The markers can then be studied in further detail. A method can also comprise the step of comparing the properties of a molecule of interest in a sample to the properties of a known material in order to identify one or more components in the sample.

Systems for Analysis of Samples

A system for differential analysis of samples is described herein. In some embodiments, the system comprises a first apparatus for separating a complex biological sample into chemical components on the basis of retention time and a second apparatus that determines the mass of each of the separated chemical components. The retention time data and mass data for each separated component are retained in a storage medium. The system includes a processing subsystem that associates or groups the separated components on the basis of properties including retention time and mass. The system also includes an output subsystem for displaying the association of the separated chemical components. In some embodiments, the first apparatus comprises a liquid chromatography column, a gas chromatography column, or a capillary electrophoresis device.

The system includes a storage medium for retaining the retention time, mass and abundance for each separated chemical component in a sample. In some embodiments, the storage medium is a computer-readable medium that stores a plurality of data objects. The stored data objects include data objects identifying the retention time for components in the sample, the m/z ratio for components in the sample, and other chemically relevant attributes of components within the sample. Chemically relevant attributes include charge states, isotope properties and adducts. In another aspect, the stored data objects contain information about peak magnitude or peak volume. The data objects to be stored on the computer-readable medium may be further selected on the basis of signal strength. In an aspect, only data objects having signal strength greater than a prescribed value are stored on the computer-readable medium. The data objects stored on the computer-readable medium can be manipulated as text. In some embodiments, data objects are stored in data base form, such that data objects identifying retention time, m/z ratio and peak magnitude are displayed as related objects in a record.

Some embodiments of this invention provide a computer-readable medium comprising executable instructions for performing the analysis methods described herein. For example, the method to be performed can be a method for dividing the mass spectral data from a sample into feature groups, each feature group relating to a compound, wherein said dividing is performed based on retention time, mass to charge ratio, and charge state. The method may further comprise allowing the user to filter in or out compounds of interest based on one or more properties selected from the group consisting of retention time, mass, isotope pattern, charge state, abundance, mass defect, and number of ions, for example. The method may be a differential profiling method, in which each sample in a collection of multiple samples is first analyzed as described above, and then the results from the multiple samples are compared to each other or one another to identify the differences.

EXAMPLES

In this disclosure, the following abbreviations have the following meanings unless indicated otherwise. Abbreviations not defined have their generally accepted meanings.

° C.=degree Celsius
hr=hour
min=minute
sec=second
mM=millimolar
µM=micromolar
nM=nanomolar
ml=milliliter
µl=microliter
nl=nanoliter
mg=milligram
µg=microgram
kDa=kiloDalton
HPLC=high performance liquid chromatography
LC=liquid chromatography
MS=mass spectrometry
MFE=Molecular Feature Extractor
LMFE=Large Molecule Feature Extractor
ppm=parts per million Example 1

Analysis of Intact Proteins

The BioRad *E. coli* standard (5 µl×0.9 mg/ml total protein) was applied to a 150×75 µm Zorbax 300SB-C18 Chip LC column. The elution solution was a gradient of Solution A and Solution B, at a flow rate of 0.4 μl/min, as follows:
Solution A: 0.1% Formic Acid
Solution B: 0.1% Formic Acid/Acetonitrile
Gradient:

| Time (min) | % B |
|---|---|
| 0 | 20% |
| 120 | 60% |
| 125 | 95% |
| 130 | 95% |
| 135 | 20% |

Figure 4:
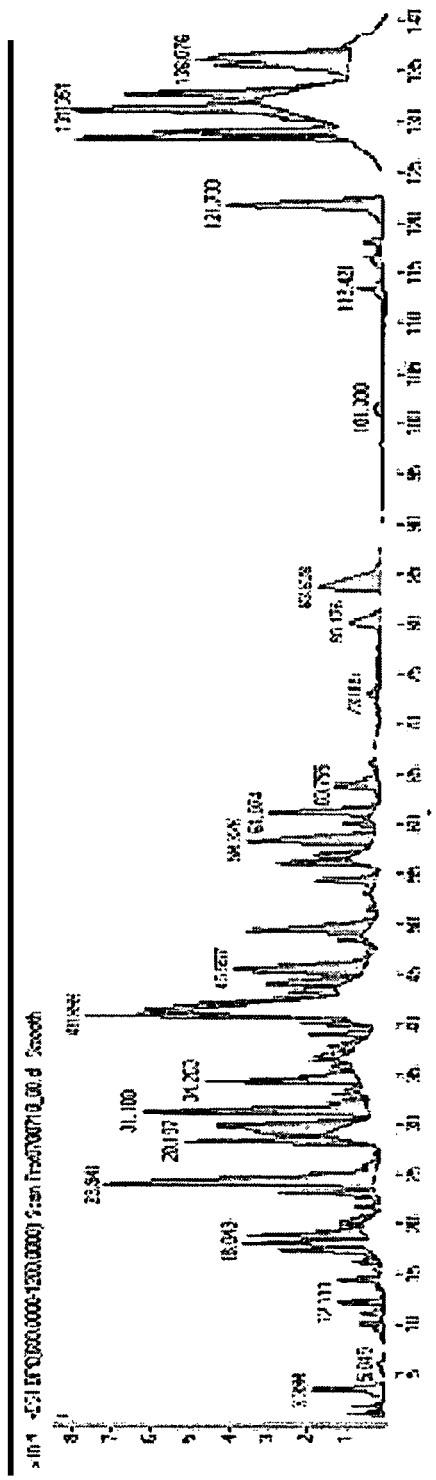
FIG. 4 shows an LC chromatogram of an E. coli sample and the results of data analyses by the maximum entropy and LMFE (large molecule feature extraction) methods, respectively.

FIG. 4 shows the LC scan of these proteins. The eluents were ionized by electrospray and analyzed with an Agilent 6210 TOF mass spectrometer. The data were analyzed independently by the maximum entropy deconvolution method and the large molecule feature extractor (LMFE) method. The maximum entropy method took 90 minutes and identified 192 compounds. In contrast, the LMFE method identified 597 compounds in 15 minutes.

REFERENCES

Ferrige et al. (1991), "Maximum entropy deconvolution in electrospray mass spectrometry," Rapid Comm. Mass Spectrom. 5:374-377.

Mann et al. (1989), "interpreting mass spectra of multiply charged ions," Anal. Chem. 61:1702-1708.

All of the publications, patents and patent applications cited above or elsewhere in this application are herein incorporated by reference in their entirety to the same extent as if the disclosure of each individual publication, patent application or patent was specifically and individually indicated to be incorporated by reference in its entirety.

The various embodiments described above are provided by way of illustration only and should not be construed to limit the invention. Those skilled in the art will readily recognize various modifications and changes that may be made to the present invention without following the example embodiments and applications illustrated and described herein, and without departing from the true spirit and scope of the present invention.

The invention claimed is:

1. A method of deconvoluting mass spectral data from a complex sample, the data comprising 3-D peaks, each 3-D peak having a retention time, m/z value and abundance; said method comprising:
identifying 3-D peaks that share a same retention time; and from the 3-D peaks sharing the same retention time, identifying a series of 3-D peaks of which the m/z values are related, said m/z values being related to one another as follows:

$$m/z = (M \pm im_a)/|i| \quad (1),$$

where
M is a positive number and represents a proposed neutral mass;
$m_a$ is the molecular weight of a charged moiety;
i is an integer;
the ± sign is + when the charged moiety carries a positive charge and − when the charged moiety carries a negative charge;

wherein said series of 3-D peaks is determined as corresponding to the same compound.

2. The method of claim 1, wherein the charged moiety is a proton.

3. The method of claim 1, further comprising filtering out 3-D peaks for which M is smaller than 5,000.

4. The method of claim 1, wherein the series of 3-D peaks is identified by:
(a) selecting two major 3-D peaks from the 3-D peaks sharing the same retention time;
(b) calculating the neutral mass (M) of the compound the series of 3-D peaks corresponds to by solving the following equations:

$m/z$ value of one of the major peaks $=(M+im_a)/|i|$, and $m/z$ value of the other of the major peaks $=(M+(i+1)m_a)/|i+1|$, where i is an integer and $m_a$ is the mass of a proton; and
(c) with the calculated neutral mass, identifying 3-D peaks corresponding to other charge states of the calculated neutral mass.

5. The method of claim 1, wherein the sample comprises intact proteins.

6. The method of claim 1, wherein the sample comprises synthetic polymers, nucleic acids or polysaccharides.

7. A computer-readable medium comprising executable instructions to perform the method of claim 1.

8. A system comprising the computer-readable medium of claim 7.

9. The system of claim 8, further comprising a mass spectrometer.

10. The system of claim 9, wherein the mass spectrometer comprises a quadrupole mass spectrometer, a time-of-flight spectrometer, or an ion trap.

11. The system of claim 9, further comprising at least one liquid chromatography or capillary electrophoresis apparatus.

12. The system of claim 8 that comprises an ion source selected from the group consisting of electrospray, matrix assisted laser desorption (MALDI), and photoionization ion sources.

13. A method for differential profiling multiple sets of mass spectral data, wherein each set of the mass spectral data is obtained from a distinct sample, the method comprising:
(a) analyzing each set of mass spectral data according to the method of claim 1;
(b) comparing the results of step (a) from different samples to identify compounds that are present in different amounts between or among the samples.

14. The method of claim 13, wherein the multiple sets of mass spectral data are obtained from samples corresponding to different stages of a disease.

15. The method of claim 13, wherein the multiple sets of mass spectral data are obtained from samples corresponding to cells or organisms that receive different drug treatments.

16. A method of analyzing a complex sample, comprising:
(a) separating the sample by liquid chromatography or electrophoresis;
(b) ionizing compounds separated in step (a) to generate ions;
(c) analyzing the ions with a mass spectrometer to generate mass spectral data; and
(d) analyzing the mass spectral data according to the method of claim 1.

* * * * *